(12) United States Patent
Hyde et al.

(10) Patent No.: US 10,278,864 B2
(45) Date of Patent: May 7, 2019

(54) SYSTEMS AND METHODS FOR CHROMATIC ABERRATION CORRECTION

(71) Applicant: Elwha LLC, Bellevue, WA (US)

(72) Inventors: Roderick A. Hyde, Redmond, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 363 days.

(21) Appl. No.: 14/520,795

(22) Filed: Oct. 22, 2014

(65) Prior Publication Data

US 2016/0113815 A1    Apr. 28, 2016

(51) Int. Cl.
    *A61F 9/008*    (2006.01)

(52) U.S. Cl.
    CPC .. *A61F 9/00804* (2013.01); *A61F 2009/0087* (2013.01); *A61F 2009/00842* (2013.01); *A61F 2009/00844* (2013.01); *A61F 2009/00872* (2013.01); *A61F 2009/00878* (2013.01); *A61F 2009/00885* (2013.01)

(58) Field of Classification Search
    CPC ........ A61F 9/00804; A61F 2009/00885; A61F 2009/00878; A61F 2009/00842; A61F 2009/0087; A61F 2/1637
    USPC .......................................................... 606/5
    See application file for complete search history.

(56) References Cited

U.S. PATENT DOCUMENTS

| 7,926,490 | B2* | 4/2011 | Dai | A61F 9/008 128/898 |
|---|---|---|---|---|
| 8,486,055 | B2 | 7/2013 | Knox et al. | |
| 8,512,320 | B1 | 8/2013 | Knox et al. | |
| 2009/0005764 | A1 | 1/2009 | Knox et al. | |
| 2011/0071509 | A1 | 3/2011 | Knox et al. | |
| 2011/0172649 | A1 | 7/2011 | Schuele et al. | |
| 2012/0249950 | A1* | 10/2012 | Dai | A61B 3/0025 351/159.74 |
| 2012/0310223 | A1 | 12/2012 | Knox et al. | |
| 2013/0226162 | A1 | 8/2013 | Knox et al. | |

FOREIGN PATENT DOCUMENTS

WO    WO-2011/085274    7/2011

OTHER PUBLICATIONS

Ding et al., "Intratissue Refractive Index Shaping (IRIS) of the Cornea and Lens Using a Low-Pulse-Energy Femtosecond Laser Oscillator", Investigative Ophthalmology & Visual Science, Dec. 2008, vol. 49, No. 12, p. 5332-5339.

(Continued)

*Primary Examiner* — Aaron F Roane
(74) *Attorney, Agent, or Firm* — Foley & Lardner LLP

(57) ABSTRACT

A system for correcting chromatic aberrations in an eye includes a diagnostic system configured to provide aberration data regarding a degree of chromatic aberration within an eye; a laser system; and a processing circuit configured to determine a diffractive lens profile to be applied to corneal tissue of the eye based on the aberration data and a desired correction of the chromatic aberration within the eye; and control operation of the laser system to apply the diffractive lens profile to the corneal tissue.

10 Claims, 6 Drawing Sheets

(56) References Cited

OTHER PUBLICATIONS

Nagy et al., "Potentiation of Femtosecond Laser Intratissue Refractive Index Shaping (IRIS) in the Living Cornea with Sodium Fluorescein", Investigative Ophthalmology & Visual Science, Feb. 2010, vol. 51, No. 2, p. 850-856.
Xu et al., "Noninvasive Intratissue Refractive Index Shaping (IRIS) of the Cornea with Blue Femtosecond Laser Light", Investigative Ophthalmology & Visual Science, Oct. 2011, vol. 52, No. 11, p. 8148-8155.

* cited by examiner

SYSTEMS AND METHODS FOR CHROMATIC ABERRATION CORRECTION

BACKGROUND

The human eye receives light rays generated by various light sources (the sun, etc.) and light rays reflected off of various objects. The light rays enter the eye through the cornea and pass through a lens that focuses the light rays at the retina at the back of the eye. Optical materials such as the cornea and the lens in the eye have different refractive indices for different wavelengths (e.g., colors) of light. As such, due to the inherent characteristics of the lens, different colors tend to focus at different convergent points, resulting in fringes of color appearing, for example, along boundaries separating dark and light objects.

SUMMARY

One embodiment relates to a system for correcting chromatic aberrations in an eye, including a diagnostic system configured to provide aberration data regarding a degree of chromatic aberration within an eye; a laser system; and a processing circuit configured to determine a diffractive lens profile to be applied to corneal tissue of the eye based on the aberration data and a desired correction of the chromatic aberration within the eye; and control operation of the laser system to apply the diffractive lens profile to the corneal tissue.

Another embodiment relates to a system for correcting chromatic aberrations in an eye, including a diagnostic system configured to provide aberration data for an eye, the aberration data including data regarding a degree of chromatic aberration within the eye and a degree of misshape of the cornea of the eye; a laser system; and a processing circuit configured to determine a diffractive lens profile to be applied to corneal tissue of the eye based on the degree of chromatic aberration and a desired correction of the chromatic aberration; determine a modified shape of the eye based on the degree of misshape of the eye; and control operation of the laser system to apply the diffractive lens profile to corneal tissue of the eye and reshape a peripheral contour of the cornea.

Another embodiment relates to a system for correcting chromatic aberrations in an eye, including a laser system; and a processing circuit configured to determine a diffractive lens profile to be applied to corneal tissue of the eye based on a degree of chromatic aberration and a desired correction of the chromatic aberration; determine a modified shape of the eye based on an achromatic aberration of the eye; and control operation of a laser system to apply the diffractive lens profile to corneal tissue of the eye and reshape the peripheral contour of the cornea.

Another embodiment relates to a method for correcting chromatic aberrations in an eye, including receiving aberration data regarding a degree of chromatic aberration within an eye; determining a diffractive lens profile to be applied to corneal tissue of the eye based on the degree of chromatic aberration and a desired correction of the chromatic aberration within the eye; and controlling operation of a laser system to apply the diffractive lens profile to corneal tissue of the eye.

Another embodiment relates to a method for correcting chromatic aberrations in an eye, including receiving aberration data for an eye, the aberration data including data regarding a degree of chromatic aberration within the eye and a degree of misshape of the cornea of the eye; determining a diffractive lens profile to be applied to corneal tissue of the eye based on the degree of chromatic aberration and a desired correction of the chromatic aberration; determining a modified shape of the eye based on the degree of misshape of the eye; and controlling operation of a laser system to apply the diffractive lens profile to corneal tissue of the eye and reshape the peripheral contour of the cornea.

Another embodiment relates to a method for correcting chromatic aberrations in an eye, including determining a diffractive lens profile to be applied to corneal tissue of the eye based on a degree of chromatic aberration; determining a modified shape of the eye based on an achromatic aberration of the eye; and controlling operation of a laser system to apply the diffractive lens profile to corneal tissue of the eye and reshape the peripheral contour of the cornea. The laser system is controlled to reshape the cornea further based on a focal shift resulting from applying the diffractive lens profile to the cornea.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
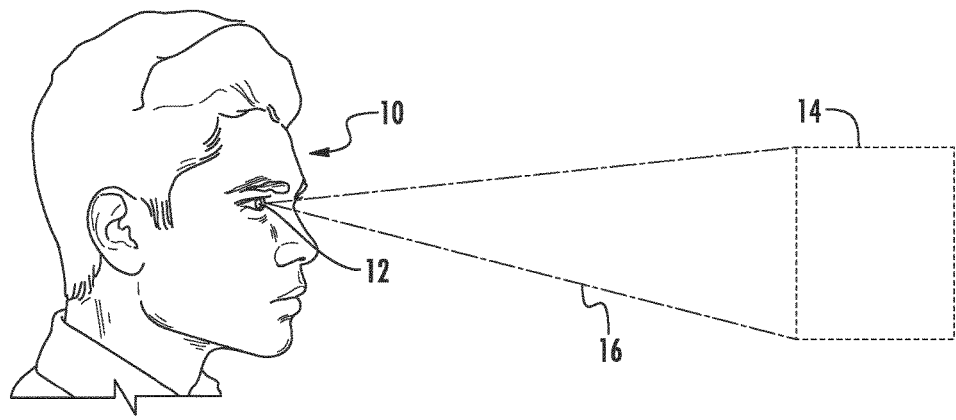
FIG. 1 is a perspective view of a human eye receiving light rays according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, various embodiments disclosed herein relate to correcting occurrences of optical aberrations within the human eye, and more specifically, to correcting chromatic and other aberrations within the human eye. The lens of the human eye is a biconvex lens, and has different refractive indices for different wavelengths (e.g., colors) of light. As such, due to the inherent characteristics of the lens, different colors tend to focus at different convergent points, resulting in fringes of color appearing, for example, along boundaries separating dark and light objects. As with the majority of optical materials, the refractive indices for materials in the eye are larger for short wavelength light (e.g., blue light) than for long wavelength light (e.g., red light). Accordingly, blue light focuses at a shorter distance within the eye than red light does. As a consequence, if one color is focused on the retina, other colors will not be. For example, if green light is focused on the retina, then red light will be focused slightly behind it, while blue light will be focused above the retina. Hence, multi-color objects are inherently somewhat blurry, and due to the nonlinearity of the dependence of refractive index with wavelength, this blurriness is generally more pronounced for blue than for other colors.

Laser eye surgery, sometimes referred to as Lasik (laser-assisted in situ keratomileusis) or laser vision correction, employs the use of a laser system to improve visual acuity of patients. Often, laser eye surgery is used to reshape the cornea (e.g., round, flatten, form a refractive lens profile, remove abnormal surfaces, etc.) in order to address various issues within the eye, including astigmatism, near- or far-sightedness, and the like. As noted below, short-pulse lasers are in some embodiments used in laser eye surgery to correct chromatic aberrations within the eye. Other laser-based corneal vision correction procedures, such as PRK (photorefractive keratectomy) may be used to implement the diffractive corrective techniques disclosed herein.

Figure 2:
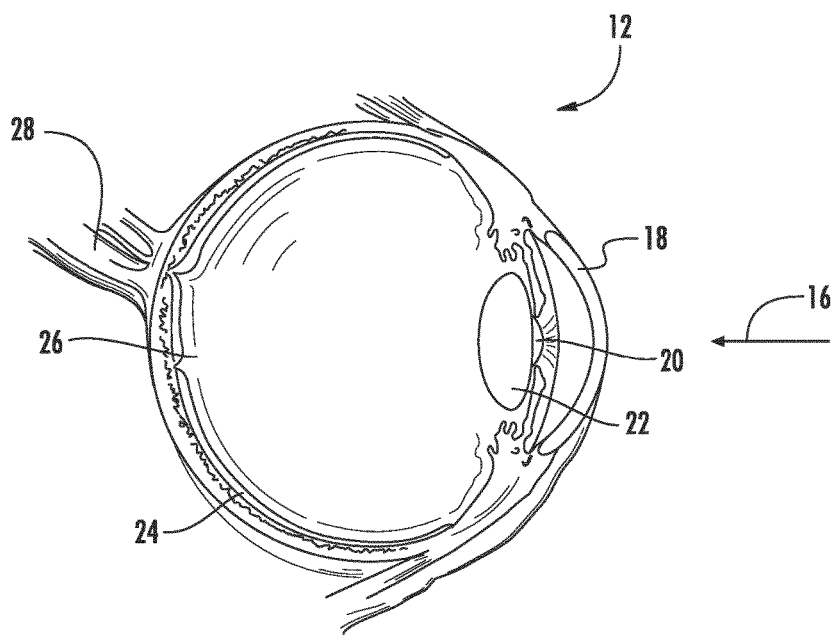
FIG. 2 is a cross-section view of a human eye according to one embodiment.

Referring now to FIGS. 1-2, eye 12 of person 10 is shown according to one embodiment. Eye 12 receives light 16 (e.g., light rays or electromagnetic radiation having wavelengths within the visible spectrum) from various sources, including sunlight, light reflected by objects such as object 14, etc. Light 16 enters eye 12 through cornea 18. Cornea 18 is a substantially transparent outer covering of the eye that bends or refracts the light. Light rays are refracted, or bent, due to differences in the refractive index of the light during its transmission, e.g., across surfaces between two differing materials, such as the front and back surfaces of cornea 18 and lens 22. From the cornea, the light passes through pupil 20 and lens 22. Lens 22 further bends or refracts light 16 such that light 16 (ideally) is focused on retina 24 at the back of the eye. Retina 24 is a relatively thin layer of tissue at the back of the eye, and includes light-sensing nerve cells concentrated in macula 26. The nerve cells convert the sensed light to electrical impulses, which are transported to the brain via optical nerve 28.

Ideally, as light passes through lens 22, the various light rays (e.g., corresponding to the different wavelengths/colors of light) focus on a single focal point. However, as noted previously, lenses inherently refract light rays of different wavelengths differently. As such, rather than converging on a single convergent focal point, light rays of different wavelengths or colors tend to converge at various different points along the optical axis of the lens. This results in optical distortion referred to as chromatic aberration. The focal point can be displaced longitudinally (i.e., longitudinal chromatic aberration) or laterally (i.e., lateral chromatic aberration). Other optical aberrations causing imperfect focusing occur within the eye, including astigmatism, coma, spherical aberration, and others. Because the refractive indices are wavelength dependent, such optical aberrations are color dependent as well. For conceptual purposes, any aberration may be split into the sum of two parts, one (the achromatic aberration) which is independent of wavelength and a second (the chromatic aberration) which encompasses the wavelength dependence. The achromatic aberration can be chosen to be the value of the aberration at a specific wavelength (e.g., for green light). The achromatic aberration can be chosen to be the average value of the aberration over a specified wavelength region (e.g., for visible light). Any reasonable choice of the reference wavelength(s) for defining the achromatic portion of an aberration is permitted; the chromatic portion is then simply the full spectrally dependent aberration minus the achromatic value.

Figure 3:
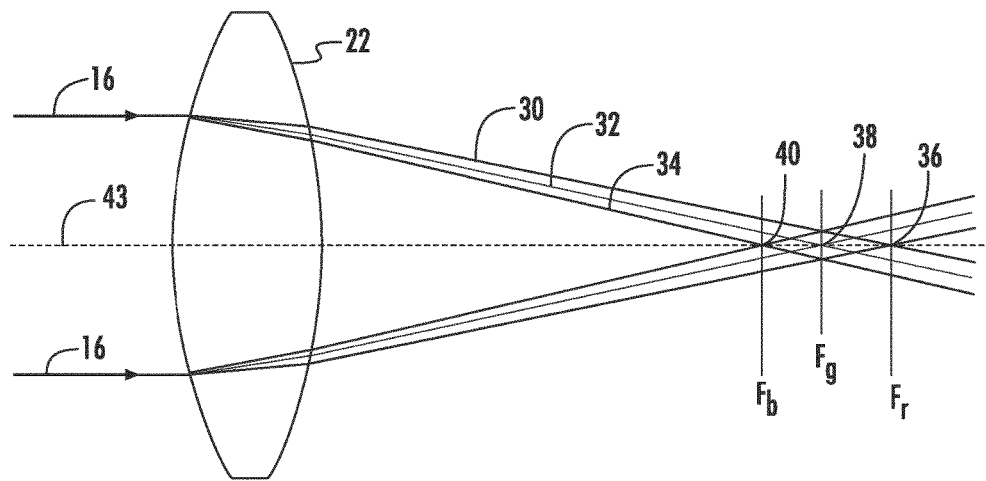
FIG. 3 is a schematic illustration of a lens of an eye and chromatic aberrations according to one embodiment.

Referring now to FIG. 3, lens 22 acting on light 16 is shown according to one embodiment. Lens 22 is a biconvex lens defining optical axis 43. While as shown in FIG. 3 lens 22 includes generally symmetric front and rear surfaces, in practice the front and rear surfaces of lens 22 are non-symmetric and/or variable to enable focusing of the human eye on objects at various distances. Light 16 enters lens 22 and is refracted toward optical axis 43. As shown in FIG. 3, red light 30 converges along optical axis 43 at focal point 36, green light 32 converges along optical axis 43 at focal point 38, and blue light 34 converges along optical axis 43 at focal point 40.

The differences in focal distances between the red, green, and blue light results from the different colors being associated with light rays of different wavelengths, and the cornea and lens having differing refractive properties for each different wavelength. For example, lens 22 has more focusing power for blue light than red light, resulting in a shorter focal distance for blue light than for red light. The resultant condition is referred to as longitudinal chromatic aberration, and results in fringes of color appearing, for example, along boundaries separating dark and light objects. Incident light 16 in FIG. 3, is illustrated as arriving along the lens's optical axis 43; in more general cases where light 16 arrives at an angle to optical axis 43, then focal points 40, 38, and 36 will be displaced sideways by different amounts, an effect referred to as lateral chromatic aberration.

Figure 4:
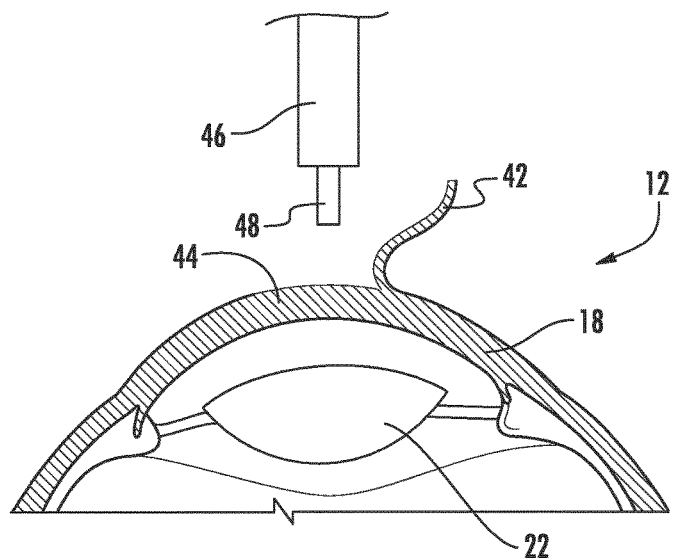
FIG. 4 is a schematic illustration of a laser and an eye according to one embodiment.

Referring to FIG. 4, in some embodiments, to address one or more optical aberrations, a laser system such as laser system 58 is used. FIG. 4 illustrates cornea 18 above lens 22, with corneal flap 42 raised and moved laterally to one side of the underlying corneal tissue 44. Laser system 58 incudes laser 46 configured to emit laser or light beam 48. In one embodiment, laser 46 is an excimer laser configured to remove (e.g., vaporize, etc.) portions of corneal tissue by, for example, using short-pulse laser emissions. According to other embodiments, other types of lasers may be utilized that are configured to act on other portions of the eye or in other manners.

Figure 5:
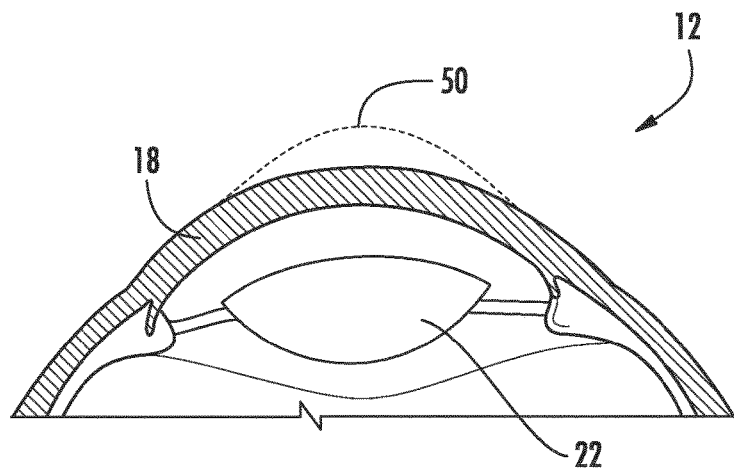
FIG. 5 is a cross-section view of a portion of an eye illustrating a reshaping of a cornea according to one embodiment.

Referring further to FIG. 4, in some embodiments, laser 46 is configured to direct light beam 48 onto corneal tissue 44 located below corneal flap 42 of cornea 18. Corneal flap 42 is a thin layer of corneal tissue temporarily moved laterally to one side of laser 46 so as to enable laser 46 to reach the underlying tissue. Through use of laser 46, corneal tissue 44 can be reshaped to address various conditions including astigmatism, near-sightedness, far-sightedness, and the like. As shown in FIG. 5, in some embodiments, laser 46 is use to reshape cornea 18 to, for example, remove irregular or undesired portions of cornea 18. For example, an undesired portion 50 of cornea 18 may be removed from cornea 18, and result in a different refractive effect for eye 12. Reshaping cornea 18 may include rounding, flattening, forming a refractive lens profile, or otherwise changing the physical shape of cornea 18.

Figure 6:
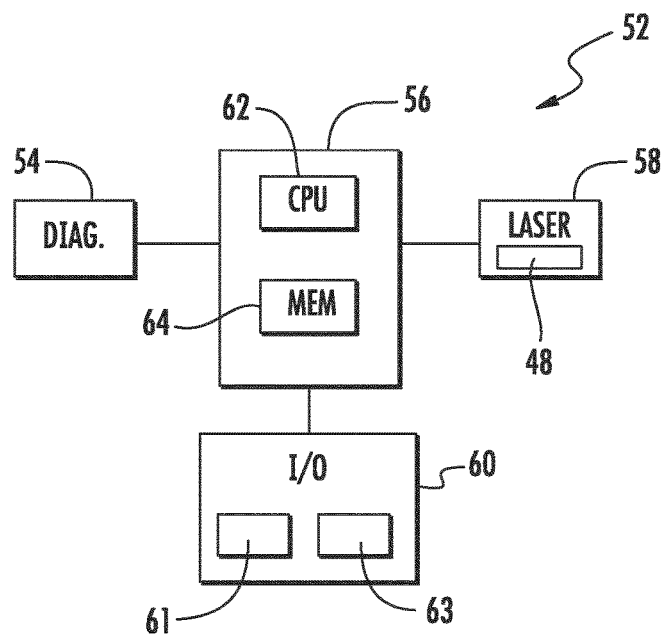
FIG. 6 is a block diagram of a control system for using a laser to apply a diffractive pattern to an eye according to one embodiment.

Referring now to FIG. 6, control system 52 for use in laser eye procedures is shown according to one embodiment. As shown in FIG. 6, control system 52 includes diagnostic system 54, processing circuit 56, and laser system 58. Control system 52 further includes input/output device 60. Diagnostic system 54, processing circuit 56, laser system 58, and input/output device 60 can communicate with each other using any suitable wired or wireless communications protocol, and may be located remotely from each other, locally with each other, integrated into a common housing or device, or be provided in any other suitable configuration.

Diagnostic system 54 is configured to assess a current state of eye 12 and identify one or more aberrations or other conditions, including chromatic aberrations and the like. In one embodiment, diagnostic system 54 is or includes an imaging device configured to map the surface curvature or other areas of the cornea or other components of the eye. For example, system 54 may be configured to provide three-dimensional (3D) images of the cornea or other portions of the eye. In some embodiments, system 54 is or includes a topography system such as a keratometry, a corneal topography, a photokeratoscopy or a videokeratography system.

In addition to one or more corneal topography systems, diagnostic system 54 may be or include other diagnostic devices configured to evaluate one or more portions of the eye, including the cornea, lens, and the like. Further, system 54 may be configured to receive inputs from a user (e.g., an ophthalmologist, etc.) regarding a visual analysis and/or examination of an eye. Such examinations can use instruments such as phoropters (for classical focal quality analysis), aberrometers (for wavefront analysis), or the like. These examinations can be performed for a single wavelength, for a simultaneous suite of wavelengths (e.g., white light), or sequentially using different colors (thereby measuring chromatic aberrations). Diagnostic system 54 forwards diagnostic data to processing circuit 56.

Referring further to FIG. 6, processing circuit 56 includes processor 62 and memory 64. Processor 62 may be implemented as a general-purpose processor, an application specific integrated circuit (ASIC), one or more field programmable gate arrays (FPGAs), a digital-signal-processor (DSP), a group of processing components, or other suitable electronic processing components. Memory 64 is one or more devices (e.g., RAM, ROM, Flash Memory, hard disk storage, etc.) for storing data and/or computer code for facilitating the various processes described herein. Memory 64 may be or include non-transient volatile memory or non-volatile memory. Memory 64 may include database components, object code components, script components, or any other type of information structure for supporting the various activities and information structures described herein. Memory 64 may be communicably connected to processor 62 and provide computer code or instructions to processor 62 for executing the processes described herein.

According to one embodiment, processing circuit 56 is configured to control operation of laser system 58. Processing circuit 56 may control operation of laser system 58 based on a variety of factors, inputs, and the like. For example, in some embodiments, processing circuit 56 controls operation of laser system 58 based at least in part on diagnostic data received from diagnostic system 54. In further embodiments, processing circuit 56 controls operation of laser system 58 based at least in part on inputs received via an input/output device such as device 60, which may be or include a manual control such as manual control 61 for laser system 58. Manual control 61 may include any appropriate control device such as a touchscreen controller, a manually-gripped controller, and the like.

According to one embodiment, processing circuit 56 operates based on a feedback loop (e.g., an open-loop feedback system). In such an arrangement, processing circuit 56 controls operation of laser system 58 to make certain modifications to an eye such as eye 12. A sensor such as sensor 63 is configured to acquire sensor data regarding the eye during operation of laser system 58. The sensor data may include data regarding modifications made to the eye using laser system 58, further modifications required to be made to the eye using laser system 58, and the like. Similarly, sensor 63 is in some embodiments further configured to acquire sensor data relating to a position, orientation, etc. of the eye. Based on the sensor data, processing circuit 56 is configured to modify, as appropriate, control of laser system 58 to provide desired results for eye 12 during a laser eye surgical procedure.

In some embodiments, laser surgery on an eye such as eye 12 includes multiple corrective procedures done during a single surgical procedure. For example, a particular patient may undergo surgery to reshape a cornea (e.g., to round, flatten, change the radius of, form a refractive lens profile, etc.) and have a diffractive lens profile applied to a surface of the cornea. Because the modifications made during a first corrective procedure (e.g., corneal reshaping) may impact the modifications necessary during a second corrective procedure (e.g., application of a diffractive lens profile), processing circuit 56, in combination with sensor 63 or similar components, may be configured to continuously or periodically monitor changes to the eye (e.g., the cornea, lens, etc.) during a first corrective procedure to determine appropriate modifications to be made during a second or subsequent corrective procedure.

Referring further to FIG. 6, as noted above, in various embodiments, laser system 58 incudes laser 46 configured to emit laser or light beam 48. In one embodiment, laser 46 is an excimer laser configured to remove (e.g., vaporize, etc.) portions of corneal tissue by, for example, using short-pule laser emissions. Laser system 58 is configured to reshape portions of the eye (e.g., the cornea, etc.) by rounding, flattening, removing particular portions, forming a refractive lens profile, and the like, to change the refractive properties of the eye. Furthermore, laser system 58 is configured to apply various diffractive patterns (e.g. simple diffraction gratings, or more general diffractive lens profiles) to portions of the eye (e.g., the cornea). According to other embodiments, other types of lasers may be utilized that are configured to act on other portions of the eye or in other manners. As noted above, laser system 58 is in some embodiments controlled by way of processing circuit 56 or another suitable laser system control mechanism.

Figure 7:
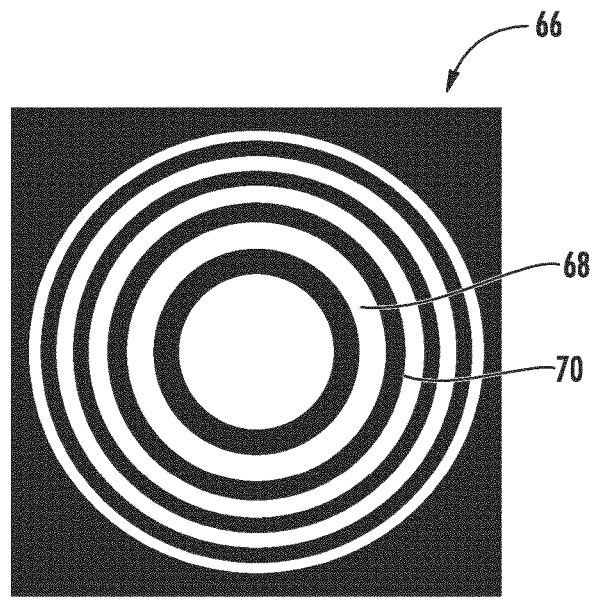
FIG. 7 is an illustration of a diffraction pattern or grating according to one embodiment.
Figure 8:
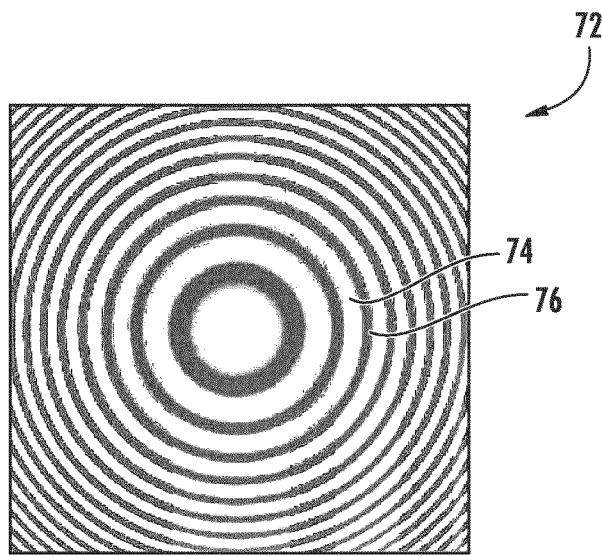
FIG. 8 is an illustration of a diffraction pattern or grating according to another embodiment.

Referring now to FIGS. 7-8, schematic representations of diffractive patterns or gratings are shown according to various alternative embodiments. The diffractive patterns may be referred to as a diffractive lens profile. As shown in FIGS. 7-8, diffractive lens profiles may include a series of radially symmetric rings, or grooves, that act to vary the transmissivity of the light (e.g., be alternatively opaque and transparent) or to vary the phase of the light (e.g., between 0 and $2\pi$) for various wavelengths of light based on the characteristic of the rings, including the width of the rings, the spacing of the rings, the depth of the rings, the slopes of the surfaces (e.g., the cornea) forming the rings, and the like. While diffractive lens profiles based on transmission variations can be emplaced on the cornea, it is generally preferable to employ diffractive lens patterns based on phase variations. These are optically more efficient (e.g., delivering more light to a given focus), and are readily implemented with LASIK or similar techniques by forming grooves in the cornea, in which the thickness variations within the grooves leads to corresponding phase variations in light passing through the grooves. Diffractive lens profiles can be described by a 2-D thickness profile along the surface in which the profile is embedded. Because diffractive lens profiles are not monotonic, but generally periodically oscillate between a minimum and maximum thickness, it is useful to describe the profiles in terms of nested grooves (each corresponding to a period of the thickness variation). The diffractive lens profile can be characterized by the curves defining the grooves (e.g., circular rings for a simple lens, or straight parallel lines for a simple grating), as well as the shapes of the thickness profile within each groove. In general, the groove curves can be considered responsible for the overall focusing of the diffraction lens (the formation of a tight focus, as well as its location and aberrations), while groove shapes (their thickness profiles) can be considered responsible for the lens efficiency (e.g., how much of the transmitted light winds up in a given focus). The grooves can take various thickness profile shapes, including square/binary, sinusoidal, sawtooth, and the like. While FIG. 7 shows a generally binary diffractive lens profile 66 having rings 68, 70, FIG. 8 shows a sinusoidal diffractive lens profile 72 having rings 74, 76. In a binary profile, thickness generally changes abruptly between 0% and 100% (or may involve N steps rather than just two), while in blazed profiles (e.g., a sinusoidal profile or a sawtooth profile) thickness changes more gradually between 0% and 100%. In a sinusoidal profile, the grooves, or rings, are formed by the sinusoidal contour extending radially outward from the center of the diffraction pattern.

In one embodiment, a general design characteristic of diffractive lens profiles is that grooves are spaced apart such that light from each groove interacts constructively with light from the other grooves. This groove coherency results in the focal length of a typical (first-order) diffractive lens being inversely proportional to wavelength. Higher order diffractive lens profiles can, in some embodiments, be used. These are physically thicker (i.e., N times the phase correction) and have wider (generally N-fold wider) grooves. Such diffractive lens profiles do, for large N, offer a more complex chromatic behavior, transitioning from the strictly linear wavelength dependence for optical power of a first-order profile, to the much less chromatic behavior of the refractive material used for the diffractive profile as N becomes very large. In the nomenclature introduced below, such diffractive lens profiles have smaller ε values than the unit value found for first-order profiles. Defining the optical power of a lens profile (diffractive or refractive) as one over its focal length (F), this can be written (for a first-order diffractive lens) as $$\Phi(\lambda)=1/F(\lambda)=\Phi_.(\lambda/\lambda)$$

where $\Phi_.$ is the optical power at a reference wavelength $\lambda$. In comparison to refractive lenses, this is a very strong chromatic sensitivity. The chromatic variation for refractive lenses is typically described in terms of the Abbe value (A) of its materials:

$$A=(N_G-1)/(n_B-n_R)$$

where $n_G$, $n_B$, and $n_R$ represent the refractive index for green, blue, and red wavelengths ($\lambda_G$, $\lambda_B$, and $\lambda_R$ respectively). Note that a small Abbe value corresponds to a large chromatic dispersion, and vice versa. For visible light, it is convenient to write the chromatic dependence (of optical properties in terms of a reduced wavelength, u:

$$u=(\lambda-\lambda_G)/\lambda_G$$

This allows the wavelength dependence of a material's refractive index $n(\lambda)$ to be written as:

$$n(\lambda)-1=(n_G-1)(1-\varepsilon u) \text{ where } \varepsilon=[\lambda_G/(\lambda_R-\lambda_B)]*(1/A)$$
$$\sim 3.5/A$$

This formulation allows general (first order) equations for the chromatic dependence of optical powers for refractive (r) and for diffractive (d) lenses to be written as:

$$\Phi_r(\lambda)=\Phi_{rG}(1-\varepsilon u)$$

$$\Phi_d(\lambda)=\Phi_{dG}(1+u)$$

Because most optical materials have Abbe values of around 30-60 (and the cornea a value of around 57), ε is typically around 0.06 to 0.12. The contrast between these small values and the large (and oppositely signed) effective value of 1.0 for diffractive lenses accounts for the attraction of using diffractive lens profiles to cancel the chromatic aberrations of the eye; a fairly weak diffractive lens is needed.

The conceptual design of a chromatically correcting diffractive lens may be illustrated by using a simplified, but instructive, model. Model the eye as having a reference, albeit chromatically dependent, optical power $\Phi_o$. One may wish to cancel its chromatic aberrations by applying a diffractive lens profile having power $\Phi_d$ to the cornea. Here, the optical powers can represent focal power (i.e., 1/F), or any other optical aberration (such as coma, astigmatism, or the like) which we wish to correct.

Eye: $\Phi_o(1-\varepsilon_o u)$

Diffractive Lens Profile: $\Phi_d(1+u)$

If the patient needs only to correct their chromatic aberration, i.e., is otherwise satisfied with the achromatic portion of the lens power $\Phi_o$, then the diffractive lens power needed to cancel the eye's chromatic aberration is $\Phi_d=\varepsilon_o\Phi_o$. Note that, because of the achromatic portion of the diffractive lens's power, the eye's resultant power would be $\Phi_o(1+\varepsilon_o)$, i.e., fully achromatic, but no longer having the desired power of $\Phi_o$.

In another situation, the patient may want to correct not just their chromatic aberration, but also change their resultant optical power to be a target value $\Phi_T$. This is in general not possible to do using only a diffractive lens profile, since the optical power after performing the chromatic correction is $\Phi_o(1+\varepsilon_o)$, which is not, in general, the desired value of $\Phi_T$. Diffractive lens profiles may be used to correct achromatic eye aberrations, i.e., setting $\Phi_d=\Phi_T-\Phi_o$. This offers the attraction that a diffractive lens profile of this optical power is much shallower (involving less laser energy to implement) than would be a more classic refractive lens profile. Here, however, the strong chromatic dependence of diffractive lenses presents a challenge; it will contribute a large chromatic aberration of $\Phi_T-\Phi_o$, generally dwarfing the eye's normal $\varepsilon_o \Phi_o$ amount of chromatic aberration. In general, therefore, corneal diffractive lens profiles are more useful in correcting the eye's chromatic aberrations than they are in correcting achromatic deficits.

It is advantageous, by applying (e.g., via a LASIK-like procedure) both a diffractive lens profile as well as a more conventional refractive modification of the cornea, to simultaneously correct both the patient's chromatic aberration, as well as achieve a target optical power, $\Phi_T$.

Eye: $\Phi_o(1-\varepsilon_o u)$

Refr: $\Phi_r(1-\varepsilon_r u)$

Diff: $\Phi_d(1+u)$

The required corrective powers are:

$\Phi_r = \{\Phi_r - (1+\varepsilon_o)\Phi_v\}/(1+\varepsilon_o)$ $\Phi_d = \{\varepsilon_r \Phi_r + (\varepsilon_o - \varepsilon_r)\Phi_o\}/(1+\varepsilon_r)$ While these models are a simplification of the actual design calculations likely to be used in implementing this approach to chromatic correction, they do illustrate the general approach and results. Use of a diffractive lens profile alone is sufficient to correct chromatic aberrations, but will generally leave a relatively small achromatic error in the resultant optical power. By combining both a refractive and a diffractive corneal correction, it is possible to correct both chromatic and achromatic aberrations (i.e., to achieve a desired achromatic target optical power). It should also be noted, that if the patient wants a non-zero chromatic variation in their target optical power, this can also be achieved by the appropriate choices of the diffractive and refractive corrections.

In an embodiment, the design of the refractive and diffractive lens profiles for corneal application can be performed with computer-based optical software. One such code is OSLO (Optics Software for Layout and Optimization) available from Lambda Research Corporation. This code allows the modeling of complex, multi-surface, optical systems, including GRIN materials (which help in the accurate modeling of the eye's lens). The code offers a default model of the human eye (including GRIN treatment of the lens). which can be customized for modeling of patient-specific eyes. OSLO allows the user to apply general diffractive lens profiles to curved material interfaces (e.g., the cornea). It should also be noted that OSLO (and other similar optical codes) are capable of optimizing optical designs to meet user-defined optical performance metrics. Hence, a user can first create a personalized model of a patient's eye, and can then use the code's optimization features to automatically find optimized diffractive and refractive corneal corrections. Other optical design software codes are available from different commercial vendors (e.g., ZEMAX, Optica, etc.) and can be used for designing diffractive and refractive corneal corrective profiles.

Referring further to FIG. 8, by controlling the diffractive lens profile applied to a portion of an eye such as the cornea, the corresponding changes to the focusing power of the eye in various wavelengths can be controlled. For example, the diffractive lens profile may be applied so as to minimize chromatic aberrations in certain wavelengths. In some embodiments, the diffractive lens profile is applied to corneal tissue so as to minimize chromatic aberrations near a single wavelength (e.g., red, green, blue, etc.) or over a range of wavelengths (red to blue, etc.). The diffractive lens profile may be applied to have a particular spacing profile between rings, a particular depth of groove, a particular slope of a sinusoidal pattern forming the grooves, and so on, in order to provide a desired change in the focusing power of the eye.

Figure 9:
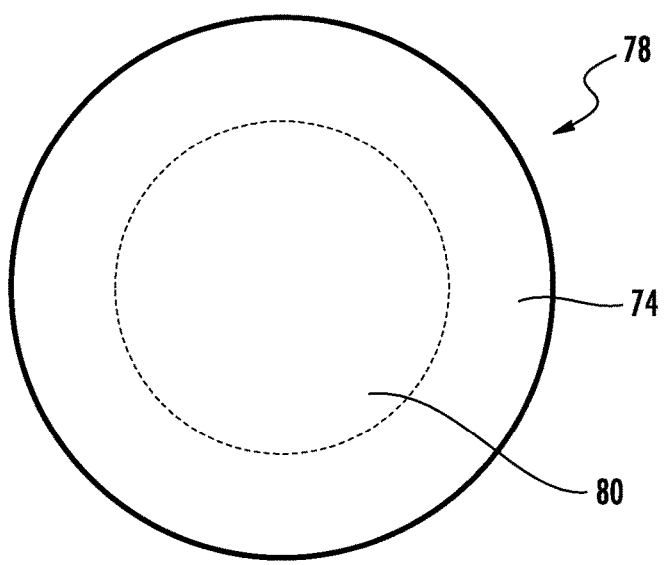
FIG. 9 is an illustration of different areas of a cornea to which a diffraction pattern or grating may be applied according to one embodiment.

In some embodiments, the diffractive lens profile is applied to substantially all of the area of the cornea through which visible light passes. In other embodiments, the diffractive lens profile is applied to only a portion of the area through which visible light passes. For example, referring to FIG. 9, area 78 of cornea 18 is shown according to one embodiment. Area 78 represents in one embodiment the area of the cornea through which visible light passes. Area 78 includes inner portion 80 and outer portion 79. In one embodiment, a diffractive lens profile is applied only to inner portion 80. In other embodiments, a diffractive lens profile is applied only to outer portion 79. The shapes and relative sizes of inner portion 80 and outer portion 79 can be varied and selected to provide a desired impact on the focusing characteristics of the eye. For example, while FIG. 9 shows a substantially circular boundary between portions 79, 80, in other embodiments, the boundary between portions 79, 80 may take other shapes, be irregular in shape, etc.

Figure 10:
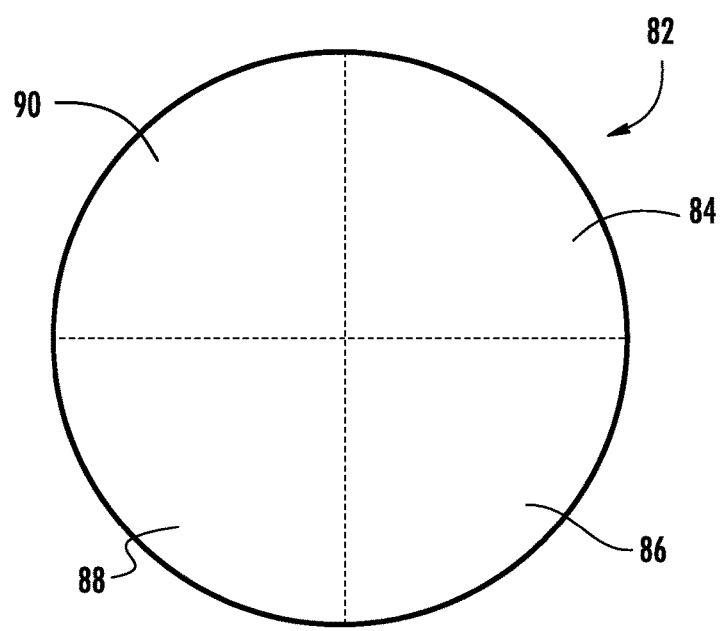
FIG. 10 is an illustration of different areas of a cornea to which a diffraction pattern or grating may be applied according to another embodiment.

Referring to FIG. 10, according to various alternative embodiments, rather than or in addition to applying a diffractive lens profile to only an inner or outer portion of the cornea, diffractive lens profiles may be selectively applied to other portions of the cornea. As shown in FIG. 10, area 82 of cornea 18 includes the area of the cornea through which visible light passes. Area 82 includes portions 84, 86, 88, and 90. While portions 84, 86, 88, and 90 are shown in FIG. 10 to be relatively equal-sized portions (e.g., quadrants, etc.) of area 82, according to various alternative embodiments, different numbers of portions may be utilized, and the portions may vary in size and shape from those depicted in FIG. 10. In one embodiment, less than all of portions 84, 86, 88, 90 include a diffractive lens profile. In some embodiments, only one of portions 84, 86, 88, and 90 includes a diffractive lens profile.

According to various alternative embodiments, in addition to applying or omitting diffractive lens profiles in various portions of the cornea such as those shown in FIGS. 9-10, the diffractive lens profile may be varied between portions of the cornea. For example, referring to FIG. 9, in one embodiment a first diffractive lens profile is applied to inner portion 80 and a second, different, diffractive lens profile is applied to outer portion 79. Similarly, referring to FIG. 10, any of portions 84, 86, 88 and 90 may include a diffractive lens profile that differs from a diffractive lens profile applied to one or more of the other portions of the cornea.

It should be noted that while various embodiments herein relate to correcting chromatic aberration within the eye by applying a diffractive lens profile to the cornea, according to various alternative embodiments, application of the diffractive lens profile may also act to correct, or at least partially correct, other optical aberrations, including near-sightedness, far-sightedness, astigmatism, and the like. As such, as described in greater detail above, the impact of multiple optical procedures may be taken into account during a single laser surgery.

Figure 11:
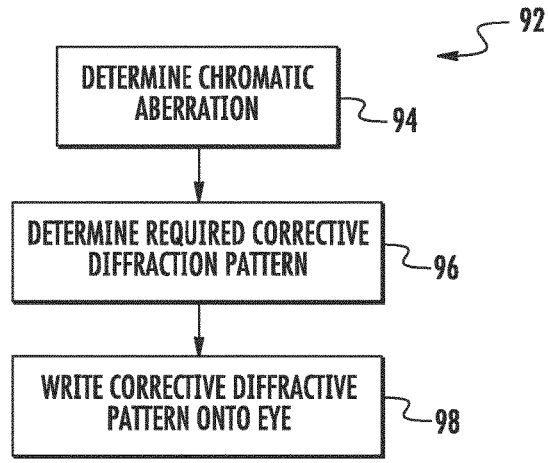
FIG. 11 is a block diagram illustrating a method of applying a diffraction pattern or grating to an eye according to one embodiment.

Referring now to FIG. 11, method 92 of correcting chromatic aberration within an eye is shown according to one embodiment. A chromatic aberration is identified (94). Identification of the chromatic aberration may include determining an extent of chromatic aberration within an eye for various wavelengths/colors. In one embodiment, the chromatic aberration is identified and evaluated by a diagnostic system such as diagnostic system 54. Based on the chromatic aberration, a corrective diffractive lens profile is determined (96). In some embodiments, the diffractive lens profile is determined by a processing circuit such as processing circuit 56 based on diagnostic or other data. The corrective diffractive lens profile is applied to the eye (98). In one embodiment, the diffractive lens profile is applied to corneal tissue by way of a laser system such as laser system 58. In some embodiments, laser system 58 is controlled by a processing circuit such as processing circuit 56.

Figure 12:
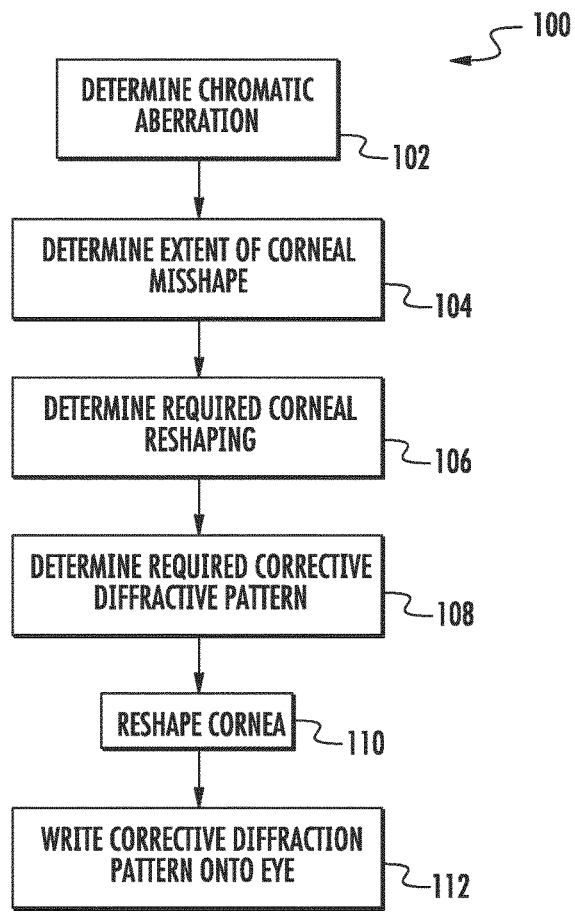
FIG. 12 is a block diagram illustrating a method of applying a diffraction pattern or grating to an eye according to another embodiment.

Referring to FIG. 12, method 100 of correcting optical aberrations within an eye is shown according to one embodiment. A chromatic aberration is identified (102). Identification of the chromatic aberration may include determining an extent of chromatic aberration within an eye for various wavelengths/colors. In one embodiment, the chromatic aberration is identified and evaluated by a diagnostic system such as diagnostic system 54. An extent of corneal misshape is determined (104). The misshape may include over-roundness, over-flatness, irregularities, or other mis-shapings of the eye. Based on the misshape of the cornea, a required corneal reshaping is determined (106). Based on the chromatic aberration, a corrective diffractive lens profile is determined (108). In some embodiments, the diffractive lens profile is determined by a processing circuit such as processing circuit 56 based on diagnostic or other data. The cornea is reshaped (110). The corrective diffractive lens profile is applied to the eye (98). In one embodiment, the cornea is reshaped and/or the diffractive lens profile is applied to corneal tissue by way of a laser system such as laser system 58. In some embodiments, laser system 58 is controlled by a processing circuit such as processing circuit 56.

It should be noted that in various alternative embodiments, method 100 may further include a feedback loop such that monitored modifications to the eye, such as rounding, flattening, application of diffractive lens profiles, etc., are used to control and/or adjust the application of additional modifications to the eye, such that the impact of past modifications are taken into account for future modifications within a single laser surgery or procedure. For example, actual or expected changes to the eye resulting from reshaping of the cornea may be taken into account when applying a diffractive lens profile or grating to the eye to obtain a desired net effect. Similarly, actual or expected changes to the eye resulting from applying a diffractive lens profile to the eye may be taken into account when reshaping the cornea to obtain a desired net effect. In some embodiments, reshaping the cornea and applying the diffractive lens profile are performed serially, while in other embodiments, portions of each procedure may be performed at the same time.

In some embodiments, the chromatic aberration being addressed can be that of overall focal power of the eye. In other embodiments, the chromatic aberration being addressed can be of a specified Zernicke aberration polynomial (e.g., a Zernicke coefficient) that provides an indication of various aberrations including astigmatism, defocus, coma, and the like. Generally, Zernicke polynomials provide indications of aberrations of the cornea or lens from an ideal spherical shape, which may result in refraction errors. In various other embodiments, other aberrations may be addressed by the systems and methods disclosed herein.

In one embodiment, the processing circuit is configured to determine an achromatic focal shift resulting from, for example, applying a diffractive lens profile to corneal tissue. The processing circuit may further control operation of a laser system such as those described herein to reshape the cornea based on the achromatic focal shift (e.g., to offset the achromatic focal shift). In some embodiments, the achromatic focal shift is determined at a particular wavelength (e.g., red, green, or blue), while in other embodiments, the achromatic focal shift is determined over a range of wavelengths (e.g., including one or more of red, green, or blue, etc.). In further embodiments, the processing circuit is configured to determine an achromatic aberrational shift resulting from applying a diffractive lens profile to corneal tissue. The processing circuit may further control operation of a laser system such as those described herein to reshape the cornea based on the achromatic aberrational shift (e.g., to offset the achromatic aberrational shift).

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for correcting chromatic aberrations in an eye, comprising:
   a diagnostic system configured to provide aberration data for an eye, the aberration data including data regarding a degree of chromatic aberration within the eye and a degree of misshape of the cornea of the eye;
   a laser system; and a processing circuit configured to:
  determine the degree of chromatic aberration within the eye and the degree of misshape of the cornea of the eye;
  determine a diffractive lens profile to be applied to corneal tissue of the eye based on the degree of chromatic aberration and a desired correction of the chromatic aberration;
  determine a modified shape of the eye based on the degree of misshape of the cornea of the eye; and
  control operation of the laser system to apply the diffractive lens profile to corneal tissue of the eye and reshape a peripheral contour of the cornea.

2. The system of claim 1, wherein the diagnostic system is further configured to provide an indication of an achromatic aberration comprising at least one of astigmatism, defocus, spherical aberration, and coma.

3. The system of claim 1, wherein the laser system is configured to reshape the cornea by at least one of flattening the cornea, rounding the cornea, forming a refraction lens profile, and removing irregularities from the cornea.

4. The system of claim 1, wherein the processing circuit is configured to determine an achromatic focal shift impact resulting from applying the diffractive lens profile to the cornea.

5. The system of claim 4, wherein the processing circuit is configured to control the laser system to reshape the cornea further based on the achromatic focal shift resulting from applying the diffractive lens profile to the cornea.

6. The system of claim 5, wherein the processing circuit is configured to control the laser system to reshape the cornea in order to offset the achromatic focal shift resulting from applying the diffractive lens profile to the cornea.

7. The system of claim 1, wherein the processing circuit is configured to determine an achromatic aberrational shift resulting from applying the diffractive lens profile to the cornea.

8. The system of claim 7, wherein the processing circuit is configured to control the laser system to reshape the cornea further based on the achromatic aberrational shift resulting from applying the diffractive lens profile to the cornea.

9. The system of claim 8, wherein the processing circuit is configured to control the laser system to reshape the cornea in order to offset the achromatic aberrational shift resulting from applying the diffractive lens profile to the cornea.

10. The system of claim 1, wherein the processing circuit is configured to control operation of the laser system to apply the diffractive lens profile to only a portion of the cornea.

* * * * *